(12) United States Patent
Jongen

(10) Patent No.: US 6,777,692 B2
(45) Date of Patent: Aug. 17, 2004

(54) METHOD AND APPARATUS FOR IRRADIATING PRODUCT PACKAGES

(75) Inventor: Yves Jongen, Louvain-la-Neuve (BE)

(73) Assignee: Ion Beam Applications S.A., Louvain-la-Neuve (BE)

(*) Notice: Subject to any disclaimer, the term of this patent is extended or adjusted under 35 U.S.C. 154(b) by 0 days.

(21) Appl. No.: 10/150,755

(22) Filed: May 17, 2002

(65) Prior Publication Data

US 2003/0089862 A1 May 15, 2003

(30) Foreign Application Priority Data

Nov. 14, 2001 (EP) .......................................... 01870243

(51) Int. Cl.⁷ ................................................ G21K 5/00
(52) U.S. Cl. .............................. 250/492.1; 250/455.11; 250/307
(58) Field of Search ........................ 250/492.1, 455.11, 250/307, 453.11, 492.21, 370.09

(56) References Cited

U.S. PATENT DOCUMENTS

| | | | |
|---|---|---|---|
| 3,390,769 A | | 7/1968 | Tatham et al. |
| 3,917,947 A | * | 11/1975 | Fenton .......................... 378/57 |
| 4,151,419 A | | 4/1979 | Morris et al. |
| 4,484,341 A | | 11/1984 | Luniewski |
| 4,770,851 A | | 9/1988 | Joslyn |
| 5,523,052 A | * | 6/1996 | Bridges et al. ................ 422/22 |
| 6,344,638 B1 | * | 2/2002 | Tomasello .................... 219/770 |
| 6,455,013 B1 | * | 9/2002 | Crihan ......................... 422/186 |
| 6,463,123 B1 | * | 10/2002 | Korenev ....................... 378/69 |
| 6,504,898 B1 | * | 1/2003 | Kotler et al. .................. 378/64 |

FOREIGN PATENT DOCUMENTS

WO    WO85/02282    5/1985

OTHER PUBLICATIONS

Bly, J.H., "Electron beam sterilization technology," *Radiat. Phys. Chem*, 14:403–414 (1979).

* cited by examiner

Primary Examiner—Nikita Wells
Assistant Examiner—Anthony Quash
(74) Attorney, Agent, or Firm—Merchant & Gould P.C.

(57) ABSTRACT

The present invention is related to an apparatus and method for irradiating product packages (1). One measures the effective dimension of a product package (1), one processes a product package (1) having everywhere an effective thickness below a predefined threshold with an e-beam source (17), and other packages with either a gas sterilisant device or an X-ray or gamma source. Packages for treating with the X-ray or gamma source are grouped in layers and stacked, in order to optimise the throughput of the apparatus.

12 Claims, 5 Drawing Sheets

METHOD AND APPARATUS FOR IRRADIATING PRODUCT PACKAGES

FIELD OF THE INVENTION

The present invention is related to the irradiation of product packages.

STATE OF THE ART

Irradiation is used to treat many types of products and articles. Irradiation is used e.g. for sterilising medical devices, or for pasteurising food. Depending on the level of dose required for achieving an effect, and the type of irradiation source available, one uses gamma rays, e-beam or x-rays. These radiation types have very different properties as to penetration in matter, and the production methods are also very different.

Document "Electron Beam Sterilization Technology" (Radiat. Phys. Chem. Vol. 14, pp. 403–414 James H. Bly) describes a facility for e-beam sterilization (see FIG. 6 of said document). E-beam irradiation sources are well know, easy and safe to operate and maintain. However, as shown on FIG. 1, penetration depth is limited to a value. This penetration depth depends on beam energy. Dose falls sharply beyond that depth. Penetration depths are given in g/cm2, corresponding to the actual depth multiplied by product density. The optimum thickness $R_{opt}$ is the depth at which the dose is equal to the dose at the surface where the electron beam enters. This $R_{opt}$ is the maximum allowable thickness of product for reaching at least a specified dose across full depth. As shown on FIG. 1, this optimum thickness is about 3.9 g/cm2 for a 10 MeV electron beam, or 3.9 cm for a product of unit density. For a product having a density of 0.5 the optimum thickness would be 7.8 cm. As an alternative, a thicker product may be treated by double-sided irradiation (FIG. 2). Product packages may be characterised by their effective thickness, defined as density multiplied by thickness for a homogenous material. For a non-homogenous material, the effective thickness is defined as the integral of the local density along the beam trajectory, and is varying along the surface of the product package. Effective thicknesses are also expressed in g/cm2.

As shown on FIG. 3, X-ray or gamma rays have a much better ability to penetrate matter. Gamma rays are produced by a radioactive isotope. A widely used isotope for such purpose is Cobalt 60. X-ray can be produced by impinging an electron beam on a conversion window made of a high Z material. In this process, a large part of the beam energy (above 90%) is lost and must be evacuated as waste heat. Therefore, the e-beam irradiation is the most efficient and economic process, provided the thickness and density of the product are not above the penetration depth. In most applications, the sizes and density of the product is known in advance, and a choice of the irradiation source is made once and for all. In the treatment of mail against biological threats, however, some letters or letter packages might contain higher density parts, including metallic pieces. In that case, irradiation by e-beam would not be effective. Depending on the required level of bacteria elimination, the required doses might be from 10 kGy to 56 kGy. These values are very high, and the treatment by X-rays, would appear to be impractical because it requires many hours for processing one package.

The treatment of mail against biological threats (e.g. anthrax) differs from other biological irradiation treatments, in that contaminants are easily made air-borne. This means that in any treatment requiring more that one pass through the beam, the possibility of recontamination or cross-contamination (from partially or non-irradiated product) is possible.

Installation for processing products by e-beam are known e.g. from the above cited document. An installation for processing either by e-beam or by X-rays is known from U.S. Pat. No. 4,484,341. In this installation, the products are recirculated in a closed path, thereby increasing the risk of cross-contamination.

Moreover, irradiation by e-beam and by X-ray is performed using the same packaging size. If that size is chosen as the optimal size for penetration by an e-beam, the same size will be far from optimal for X-ray, most of the energy traversing the product and being wasted in the background. If the size is chosen as the optimal size for X-ray, the e-beam will not penetrate the full product depth.

As an alternative to sterilisation by irradiation, it is known to sterilise products by submitting said products to a sterilant gas. Ethylene oxide or chlorine dioxide are gasses used in such methods. An example of such a method is given in U.S. Pat. No. 4,770,851. These methods have the drawback that they need a long processing time, including a pre-processing and post-processing. Moreover the gases that are used are highly toxic and dangerous.

Therefore none of these installations have the capability of treating products of different densities with acceptable throughput, and under the right security conditions.

AIMS OF THE INVENTION

The present invention aims to provide an irradiation apparatus and method allowing to treat a flow of product packages having a density unknown in advance, with the capability to achieve a minimal dose, without impairing throughput and processing time, and minimising risks of contaminating treated products by non-treated or partially treated products. These goals are particularly critical for treating mail against potential biological threats, such as anthrax.

SUMMARY OF THE INVENTION

The present invention is related to a method for irradiating product packages, comprising the steps of:
pre-defining a threshold of maximum effective dimension;
measuring the maximum effective dimension of a product package;
comparing said maximum effective dimension to the threshold;
directing said product package either into a first processing unit or into a second processing unit for sterilising said product package, depending on the effective dimension of the product package, said product package being directed into the first processing unit wherein the product package is sterilised with an electron-beam if its maximum effective dimension is everywhere under the threshold, or said product package being directed into the second processing unit wherein the product package is sterilised with alternative sterilization means, if the maximum effective dimension of the product package has at least an area with an effective dimension above the threshold.

It is meant by effective dimension the effective thickness measured along the direction of the electron-beam.

According to one preferred embodiment, the alternative sterilisation means are a gas sterilisation process.

According to one preferred embodiment, the alternative sterilisation means are an X-ray or gamma irradiation process.

Preferably, product packages having at least an area with an effective dimension above said threshold are grouped in arrays, a number of arrays are stacked, and said stack is irradiated from the side by an X-ray or gamma source. The stack is rotated in front of the X-ray or gamma source during irradiation, thereby improving the uniformity of the dose throughout the volume.

Preferably, sterilising a package with an e-beam in the first processing unit source is performed by an e-beam directed along the shortest dimension of the trays, i.e. from above or from below, for trays lying flat on a conveyor system.

The invention also pertains to an apparatus for irradiating product packages, comprising an irradiation source, a shielding, comprising an entry maze, an exit maze, and a conveyor device, a detection device for detecting product packages having everywhere an effective dimension below some threshold, means for directing said product packages to an e-beam source, means for directing other product packages to alternative means. Said alternative means may be a gas sterilant device or an X-ray or gamma irradiation device.

The apparatus may comprises means for grouping packages having at least an area with an effective dimension above said threshold in arrays, for stacking a number of said arrays, and for irradiating said stack from the side by an X-ray or gamma source. The apparatus may comprise a turntable for rotating said stack during irradiation.

The threshold is preferably comprised between 1 and 6 g/cm2, depending on the beam energy.

The present invention is also related to the use of an irradiation apparatus for creating both an e-beam in a first processing unit and an X-ray beam or gamma-beam in a second processing unit and for irradiating product packages with either said electron-beam or said X-ray beam or gamma-beam at least depending upon whether the maximum effective dimension of said product package is below or above a predefined threshold, respectively.

SHORT DESCRIPTION OF THE DRAWINGS

DETAILED DESCRIPTION OF THE INVENTION

Figure 1:
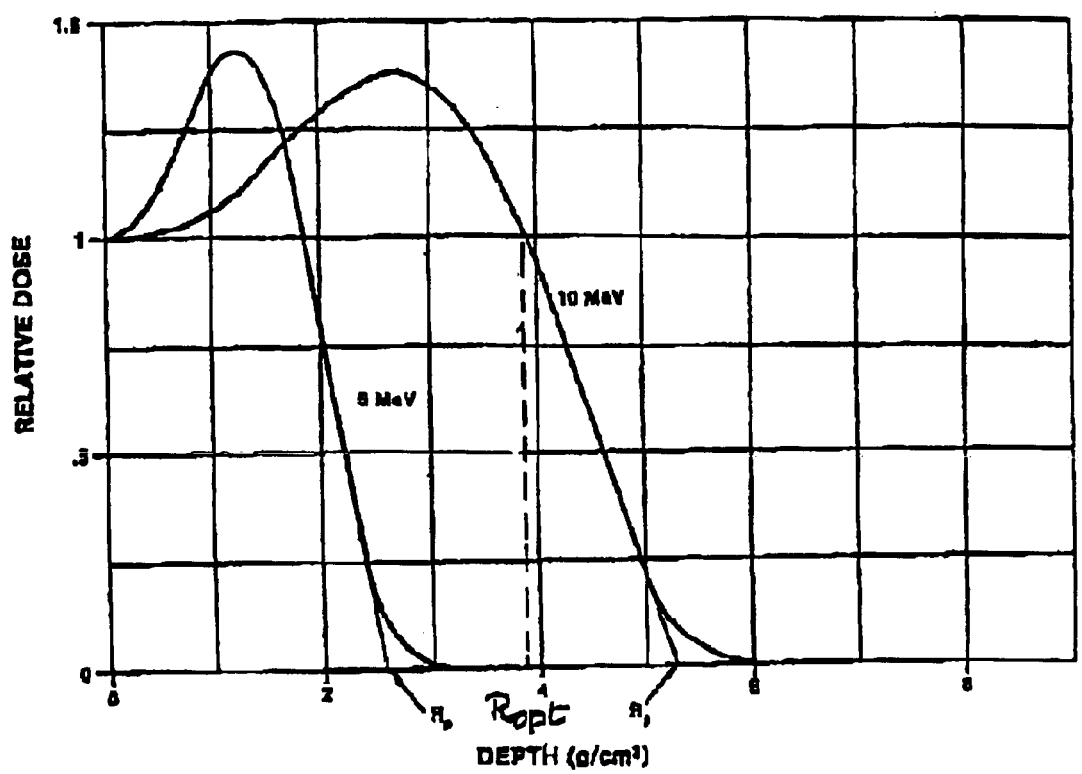
FIG. 1 represents penetration of e-beam in matter.
Figure 2:
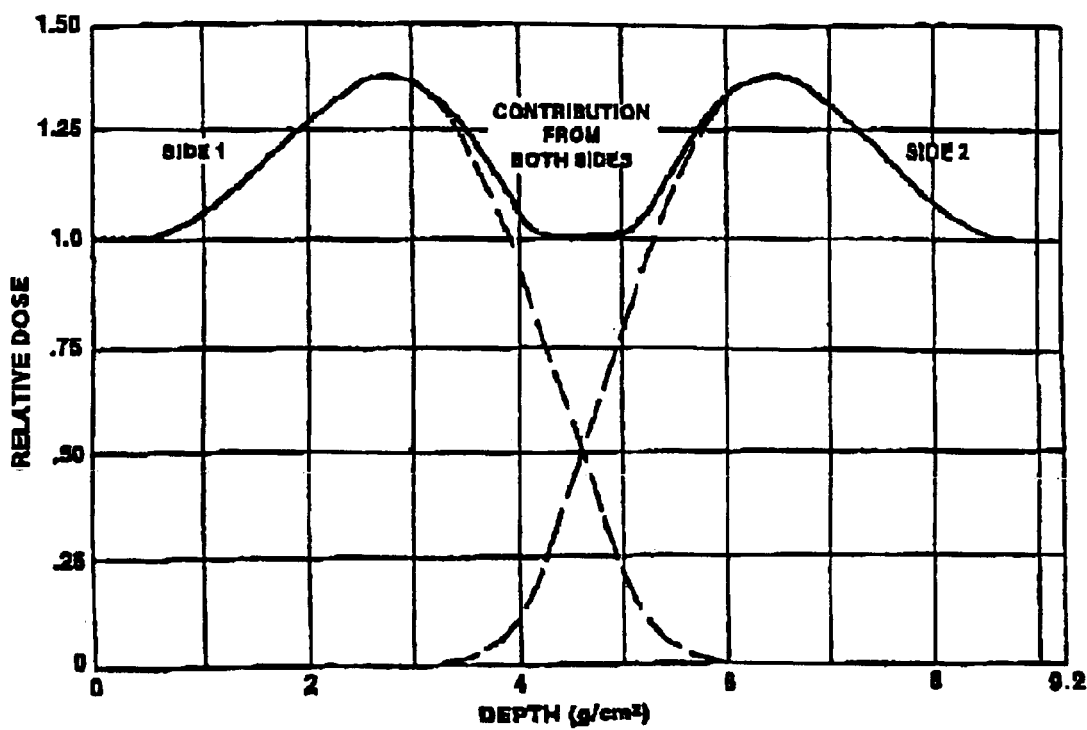
FIG. 2 represents penetration of e-beam in matter in a double side irradiation system.
Figure 3:
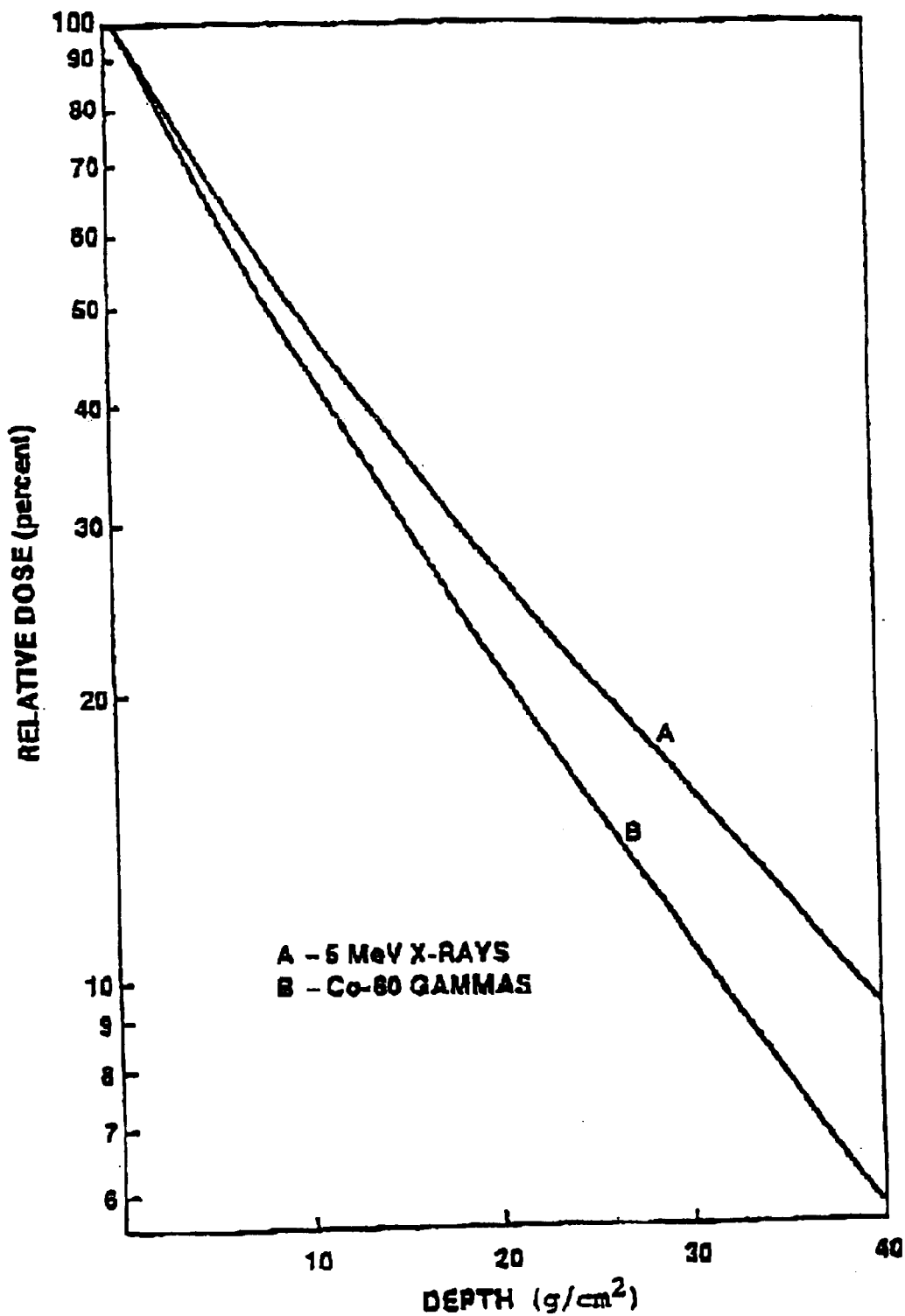
FIG. 3 represents penetration of X-rays and gamma rays in matter.
Figure 4:
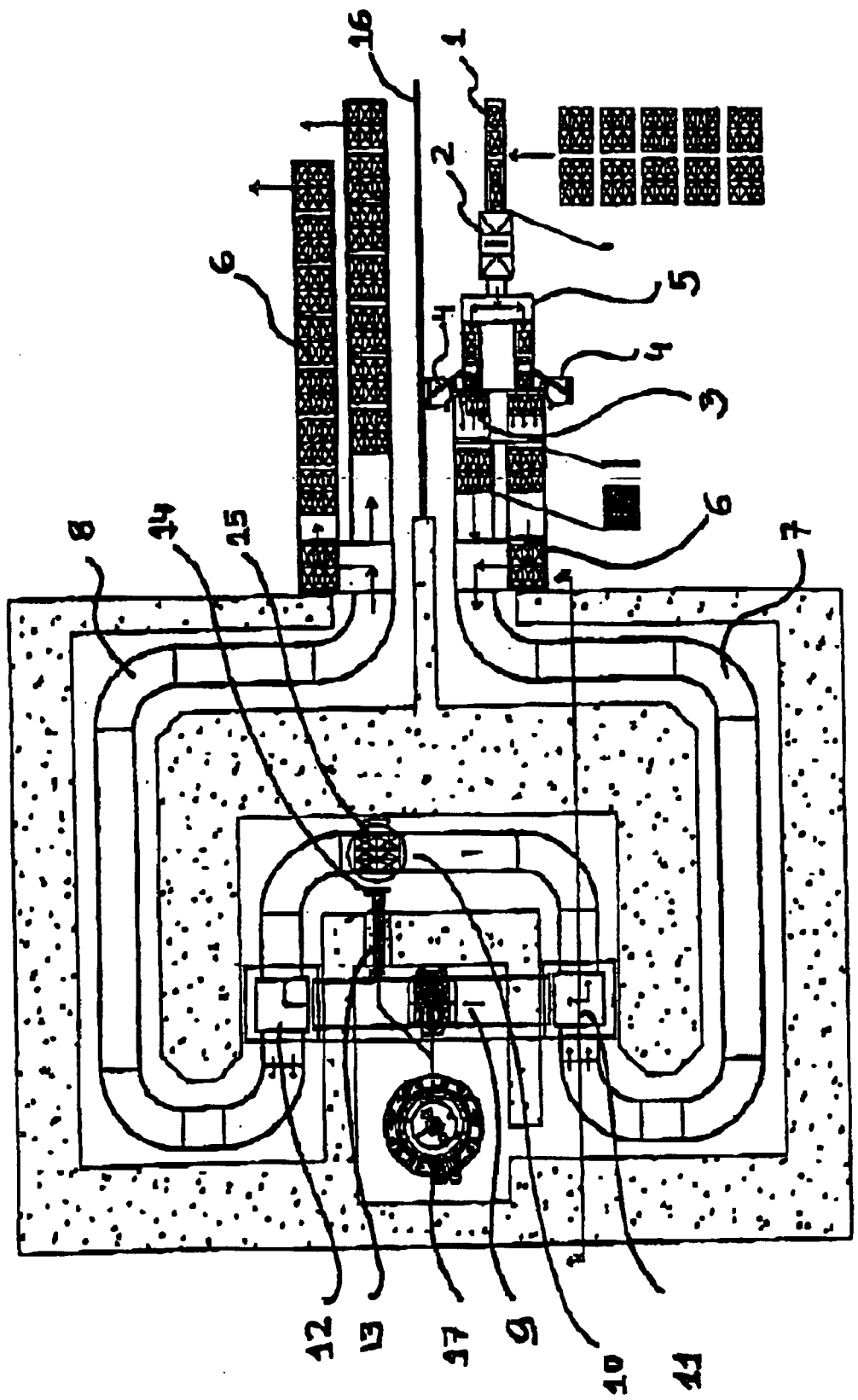
FIG. 4 represents a top view of an apparatus according to the invention.

The present invention concerns an apparatus and method for irradiation of products. FIG. 4 shows a top view of the complete apparatus. Products to be irradiated arrive in packages, like trays 1. Typical trays used by the US Post Service are 610 mm long (24 inches), 292 mm wide (11½ inches) and 133 mm high (5¼ inches).

Trays 1 are put on the entry conveyor of a detection device 2. The detection device performs the function of measuring maximum effective thickness of the trays 1. The detection device may be an X-ray inspection system such as those used in the food industry or for checking luggage at the airports. These devices may use an X-ray tube having an energy in the range of 50 kV-200 kV. The imaging device may be a linear diode array, with phosphor screen, or a CCD camera. Suitable devices are those provided by Perkin Elmer (Linescan 107) or by LIXI, Inc. (FIS Series Inspection System). The company Detection Technology, Inc. provides linear arrays of x-ray detectors (X-scan). At the exit of the detection device 2, a diverter 5 directs trays having at least an area with an effective thickness above a given threshold to the X-ray processing line (right hand side) and trays 1 having everywhere an effective thickness below said threshold to the e-beam processing line (left hand side). This diversion may be performed by a piston arm pushing trays to the side, or by driving a conveyor in the appropriate direction.

The threshold is chosen so that the effective thickness measured for the tray 1 is below the optimum thickness $R_{opt}$ for the given energy. Optimum thicknesses depend on beam energy and are 2 g/cm2, 3.9 g/cm2, 4.8 g/cm2 for 5, 10 and 12 Mev, respectively, as stated in ASTM E 1649.

At the entrance of the X-ray processing line, a palletising machine 3 performs the function of placing trays 1 as a three by two array on slave trays 6, and stacking a number of such arrays vertically. The trays 1 are lined up and stacked by a robotic arm 4. The number of layers of such a stack is limited by the vertical scan height of the X-ray line. However, in order to reduce delays, the decision may be taken to start processing of an incomplete stack. In that case, the vertical scanning height of the beam for the X-ray irradiation may be adapted so as to correspond to the actual stack height. In an alternate embodiment of the invention, the stacks are brought to a gas sterilant device.

At the entrance of the e-beam processing line, trays 1 are grouped in a three by two array on slave trays 6, but in only one layer. The width of three trays 1 side by side is 879 mm which is a convenient value for an e-beam scan horn 13 and 18.

Both the path for X-ray processing and the path for e-beam processing share a common entry maze 7 and a common exit maze 8 into and out of the irradiation rooms.

Figure 5:
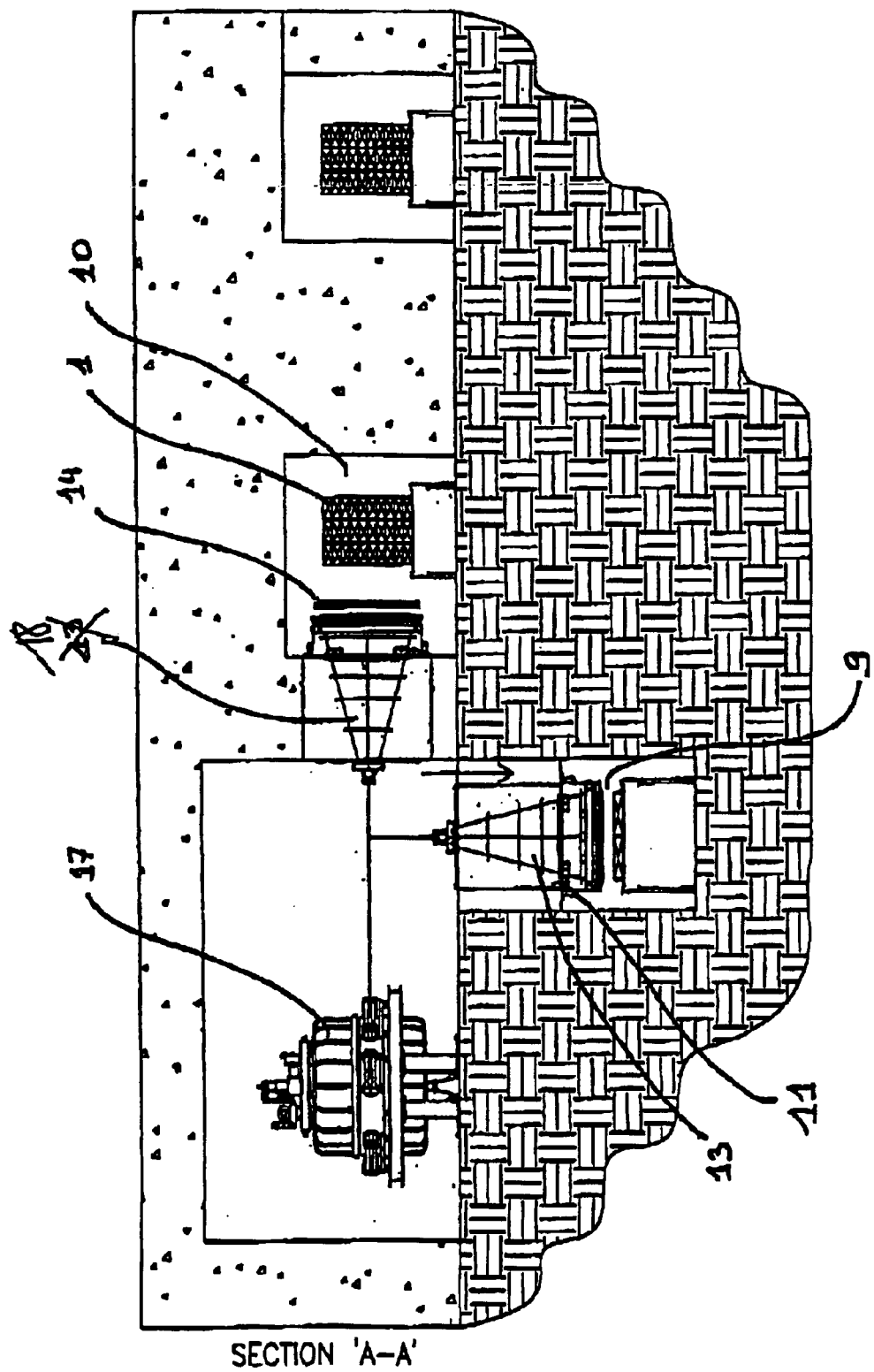
FIG. 5 represents a sectioned view of the apparatus as seen through section A'—A' in FIG. 4.

The e-beam irradiation room 9 is located on level −1, as depicted on FIG. 5. A lowering device 11 and elevator 12 bring the slave trays 6 down to the e-beam irradiation room and back up again. In the e-beam irradiation room 9, the product packages are irradiated from above.

The X-ray irradiation room 10 is located on level 0. A scan horn 18 produces a horizontal electron beam scanned in a vertical plane. A conversion window 14 made of a high-Z material performs the function of converting the energy of the electrons to X-rays, by bremsstrahlung. For treating the pallets to full depth, pallets are put on a turntable 15, and turned during the number of turns required for reaching the required dose.

The irradiation source 17 is a Rhodotron. The beam is either directed to the e-beam scan horn 13 and irradiation room 9 with a bending dipole magnet or to the X-ray scan horn 18 and irradiation room 10 with another set of bending magnets.

Outside the shielding, a separation wall 16 separates the untreated product in the loading area from the treated products in the unloading area.

Using the apparatus and method of the invention, the most efficient path, i.e. the e-beam path, is used for processing the majority of the trays. These are treated by a beam directed along the shortest dimension of the tray 1. In case the effective thickness of a set of packages, as measured by the detection device 2, is above the optimum thickness $R_{opt}$, the set of packages may be flipped over, for performing double-sided irradiation.

The invention allows to achieve throughput and to guarantee minimal dose, even under the very high constraints required for treating mail against biological threats.

The invention is not to be construed as limited to the above detailed description. More specifically, in an alternate configuration, the e-beam conveyor may be on level 0, as the detection device 2 and palettising machine 3, the X-ray conveyor being on level 1. In this configuration, only the product stacks for x-ray processing have to be brought up and down again after irradiation. The Rhodotron is on level 1. In another variation, another electron accelerator, such as a Dynamitron may replace the Rhodotron.

What is claimed is:

1. A method for irradiating product packages, comprising the steps of:
   pre-defining a threshold of maximum effective dimension;
   measuring the maximum effective dimension of a product package;
   comparing said maximum effective dimension to said threshold;
   directing said product package either into a first processing unit or into a second processing unit for sterilising said product package, depending on the effective dimension of the product package, said product package being directed into the first processing unit wherein the product package is sterilised with an electron-beam if the maximum effective dimension of said product package is under the threshold, or said product package being directed into the second processing unit wherein the product package is sterilised with alternative sterilisation means, if the product package has at least an area with an effective dimension above the threshold.

2. The method according to claim 1, wherein the alternative sterilisation means are a gas sterilisation process.

3. The method according to claim 1, wherein processing a package with an e-beam source is performed by an e-beam directed along the shortest dimension of the package.

4. The method according to claim 1, wherein the alternative sterilisation means are an X-ray or gamma irradiation process.

5. The method according to claim 4, wherein product packages having at least an area with an effective dimension above said threshold are grouped in arrays, a number of arrays are stacked, and said stack is irradiated from the side by an X-ray or gamma source.

6. The method according to claim 5, wherein said stack is rotated in front of the X-ray or gamma source during irradiation.

7. An apparatus for irradiating product packages, comprising an irradiation source, a shielding, comprising an entry maze, an exit maze, and a conveyor device comprises:
   a detection device for detecting product packages having everywhere an effective dimension below some threshold;
   means for directing product packages having everywhere an effective dimension below said threshold to an e-beam source;
   means for directing other product packages having at least an area with an effective dimension above said threshold to alternative means.

8. The apparatus according to claim 7 wherein said alternative means are a gas sterilant device.

9. A method or apparatus according to claim 7 wherein said threshold is comprised between 1 and 6 $g/cm^2$.

10. The apparatus according to claim 7 wherein said alternative means are an X-ray or gamma irradiation device.

11. The apparatus according to claim 10 further comprising a means for grouping packages having at least an area with an effective dimension above said threshold in arrays, for stacking a number of said arrays, and for irradiating said stack from the side by an X-ray or gamma source.

12. The apparatus according to claim 11 further comprising a turntable for rotating said stack during irradiation.

* * * * *